US005554532A

United States Patent [19]

Matsuyama et al.

[11] Patent Number: 5,554,532
[45] Date of Patent: Sep. 10, 1996

[54] BACTERIA USEFUL FOR PRODUCTION OF OPTICALLY ACTIVE 3-PHENYL-1,3-PROPANEDIOL

[75] Inventors: Akinobu Matsuyama; Michio Ito, both of Arai; Yoshinori Kobayashi, Joetsu; Naoki Kawada, Tsukuba, all of Japan

[73] Assignee: Daicel Chemical Industries, Ltd., Osaka, Japan

[21] Appl. No.: 224,303

[22] Filed: Apr. 7, 1994

Related U.S. Application Data

[62] Division of Ser. No. 844,609, Apr. 7, 1992, Pat. No. 5,356,812.

[30] Foreign Application Priority Data

Aug. 10, 1990 [JP] Japan .................................. 2-211861
Oct. 15, 1990 [JP] Japan .................................. 2-276101
Jul. 4, 1991 [JP] Japan .................................. 3-164354

[51] Int. Cl.$^6$ .............................. C12N 1/12; C12N 1/20
[52] U.S. Cl. ........................................ 435/252.1; 435/280
[58] Field of Search ................................ 435/280, 253.2, 435/252.1, 880, 874

[56] References Cited

U.S. PATENT DOCUMENTS

| 4,362,814 | 12/1982 | Sykes et al. | 435/119 |
|---|---|---|---|
| 4,912,042 | 3/1990 | Laumen | 435/145 |
| 4,921,798 | 5/1990 | Boaz | 435/146 |

FOREIGN PATENT DOCUMENTS 0317998  5/1989  European Pat. Off. .

OTHER PUBLICATIONS

Catalogue of Bacteria and Phages, Eighteenth Edition, 1992, published by American Type Culture Collection (ATCC), pp. 288, 289.

Bergey's Manual of Systematic Bacteriology, vol. 1, Edited by Noel R. Krieg, pp. 477–484.

Chemical Abstrcts, vol. 117, No. 1, Jul. 6, 1992, Columbus, Ohio, US; abstract No. 6149m, Akikazu Matsuyama et al. "Manufacture of optically active 3–phenyl–1,3–propanediol with bacteria".

Chemical Abstracts, vol. 117, No. 17, Oct. 26, 1992, Columbus, Ohio, US; abstract No. 169594s, Kazumasa Otsubo et al. "Manufacture of optically active 1,3–propanediols".

Chemical Abstracts, vol. 118, No. 11, Mar. 15, 1993, Columbus, Ohio, US; abstract No. 100550c, Kazumasa Otsubo et al. "Manufacture of (S)–3–phenyl–3–propanols from racemic 3–phenyl–3–propanols with microorganisms".

Grant & Hackh's Chemical Dictionary p. 162 (1989).

*Primary Examiner*—Michael G. Wityshyn
*Assistant Examiner*—Sandra Saucier
*Attorney, Agent, or Firm*—Spencer & Frank

[57] ABSTRACT

A microorganism or a preparation thereof is permitted to act on a mixture of enantiomers of 3-phenyl-1,3-propanediol, and the residual optically active 3-phenyl-1,3-propanediol is harvested. The genera of those microorganisms which are able to leave (R)-3-phenyl-1,3-propanediol include Candida, Hansenula, Rhodotorula, Protaminobacter, Aspergillus, Alternaria, Macrophomina, Preussia and Talaromyces. The genera of those microorganisms which are able to leave (S)-3-phenyl-1,3-propanediol include Candida, Geotrichum, Leucosporidium, Pichia, Torulaspora, Trichosporon, Escherichia, Micrococcus, Corynebacterium, Gordona, Rhodococcus, Aspergillus, Emericella, Absidia, Fusarium, Dactylium, Serratia and Pseudomonas.

4 Claims, No Drawings

5,554,532

BACTERIA USEFUL FOR PRODUCTION OF OPTICALLY ACTIVE 3-PHENYL-1,3-PROPANEDIOL

This is a division of application Ser. No. 07/844,609 filed Apr. 7, 1992, now U.S. Pat. No. 5,356,812.

TECHNICAL FIELD

The present invention relates to a process for producing optically active 3-phenyl-1,3-propanediol. More particularly, the invention relates to a process for producing optically active 3-phenyl-1,3-propanediol characterized by permitting a microorganism or a preparation thereof to act on a mixture of enantiomers of 3-phenyl-1,3-propanediol and harvesting the residual optically active 3-phenyl-1,3-propanediol.

Optically active 3-phenyl-1,3-propanediol is an important intermediate for the synthesis of various medicinal compounds.

BACKGROUND ART

For the production of optically active 3-phenyl-1,3-propanediol, there is known a position-selective chemical reduction of 2,3-epoxycinnamyl alcohol [J. Org. Chem., 53(17), 4081 (1988)] as well as a chemical reduction of optically active 3-phenyl-3-hydroxy-propionic acid [Tetrahedron Lett., 26(3), 351 (1985) and U.S. Pat. No. 4,921,797].

However, the former process is not fully satisfactory in position selectivity and in terms of chemical purity. The latter process is also disadvantageous in that the optically active organic acid must be resolved with an optical resolution reagent beforehand and that the optical purity of the product optically active compound is low.

Under the circumstances, the establishment of an economical and expedient process for production of optically active 3-phenyl-1,3-propanediol of high optical purity has been demanded.

DISCLOSURE OF INVENTION

It is an object of the present invention to provide a process for producing optically active 3-phenyl-1,3-propanediol of high optical purity expediently and efficiently with the aid of a microorganism.

It is another object of the invention to provide a commercially useful process for producing optically active 3-phenyl-1,3-propanediol.

It is a further object of the invention to provide an efficient process for producing (R)-3-phenyl-1,3-propanediol or (S)-3-phenyl-1,3-propanediol with the aid of a microorganism.

The present inventors were interested in the utilization of a microorganism for the economical and expedient production of optically active 3-phenyl-1,3-propanediol of high optical purity and performed an extensive screening of microorganisms, mostly isolates from the soil, to find strains suited for the above purpose. As a consequence, they discovered that certain strains selected from certain genera and species of microorganisms act on a mixture of enantiomers of 3-phenyl-1,3-propanediol to leave either (R)-3-phenyl-1,3-propanediol or (S)-3-phenyl-1,3-propanediol. The present invention has been accomplished on the basis of the above finding.

The microorganisms to be employed in accordance with the invention may be any strain of microorganism that is able to act on a mixture of enantiomers of 3-phenyl-1,3-propanediol to leave either (R)-3-phenyl-1,3-propanediol or (S)-3-phenyl-1,3-propanediol.

The genera of those microorganisms which leave (R)-3-phenyl-1,3-propanediol include, among others, Candida, Hansenula, Rhodotorula, Protaminobacter, Aspergillus, Alternaria, Macrophomina, Preussia and Talaromyces.

The genera of those microorganisms which leave (S)-3-phenyl-1,3-propanediol include, among others, Candida, Geotrichum, Leucosporidium, Pichia, Torulaspora, Trichosporon, Escherichia, Micrococcus, Corynebacterium, Gordona, Rhodococcus, Aspergillus, Emericella, Absidia, Fusarium, Dactylium, Serratia and Pseudomonas.

Such a microorganism is generally grown in a culture medium and, then, submitted to the reaction with a mixture of enantiomers of 3-phenyl-1,3-propanediol. A preparation of such microorganism may instead be used in the reaction with a mixture of enantiomers of 3-phenyl-1,3-propanediol. Preferably the mixture of enatiomers is racemic 3-phenyl-1,3-propanediol.

DETAILED DESCRIPTION OF THE INVENTION

The microorganism to be used in accordance with the present invention may be any strain of microorganism that selectively utilizes one or the other enantiomer of 3-phenyl-1,3-propanediol and leaves the optically active (R) or (S) compound intact.

As such a microorganism, there may be employed any strain of microorganism that is able to act on a mixture of enantiomers of 3-phenyl-1,3-propanediol to selectively leave (R)-3-phenyl-1,3-propanediol, said strain of microorganism being selected from the group of microorganisms belonging to the genus Candida, the genus Hansenula, the genus Rhodotorula, the genus Protaminobacter, the genus Aspergillus, the genus Alternaria, the genus Macrophomina, the genus Preussia and the genus Talaromyces; or any strain of microorganism that is able to act on a mixture of enantiomers of 3-phenyl-1,3-propanediol to selectively leave (S)-3-phenyl-1,3-propanediol, said strain of microorganism being selected from the group of microoganisms belonging to the genus Candida, the genus Geotrichum, the genus Leucosporidium, the genus Pichia, the genus Torulaspora, the genus Trichosporon, the genus Escherichia, the genus Micrococcus, the genus Corynebacterium, the genus Gordona, the genus Rhodococcus, the genus Aspergillus, the genus Emericella, the genus Absidia, the genus Fusarium, the genus Dactylium, the genus Serratia and the genus Pseudomonas.

As typical examples of the strain of microorganism that is able to act on a mixture of enantiomers of 3-phenyl-1,3-propanediol to leave (R)-3-phenyl-1,3-propanediol, there may be mentioned the genus Candida: *Candida lambica* DSM 70090, etc., the genus Hansenula: *Hansenula minuta* DSM 70274, etc., the genus Rhodotorula: *Rhodotorula rubra* AHU 3945, AHU 3948, etc., the genus Protaminobacter: *Protaminobacter ruber* IAM 1081, etc., the genus Aspergillus: *Aspergillus niger* IFO 4414, *Aspergillus ficuum* IFO 4318, etc., the genus Alternaria: *Alternaria kikuchiana* IFO 5778, etc., the genus Macrophomina: *Macrophomina phaseoli* IFO 6696, etc., the genus Preussia: *Preussia terricola* IFO 7893, etc., and the genus Talaromyces: *Talaromyces flavus* var. flavus IFO 7231, etc., and the like.

At least one strain of microorganism among them can be employed.

As typical examples of the strain of microorganism that is capable of acting on a mixture of enantiomers of 3-phenyl-1,3-propanediol to leave (S)-3-phenyl-1,3-propanediol, there may be mentioned the genus Candida: *Candida pintolopesii* var. pintolopesii IFO 0729, etc., the genus Geotrichum: *Geotrichum candidum* IFO 4597, IFO 4598, IFO 5368, IFO 31810, JCM 1747, JCM 5222, *Geotrichum fermentans* JCM 2467, JCM 2468, *Geotrichum klebahnii* JCM 2171, etc., the genus Leucosporidium: *Leucosporidium scottii* IFO 1923, etc., the genus Pichia: *Pichia quercuum* DSM 70386, etc., the genus Torulaspora: *Torulaspora delbrueckii* IFO 0955, etc., the genus Trichosporon: *Trichosporon capitatum* IFO 1197, etc., the genus Escherichia: *Escherichia coli* IFO 3543, etc., the genus Micrococcus: *Micrococcus luteus* IFO 12708 etc., the genus Corynebacterium: *Corynebacterium hoagii:* JCM 1319, etc., the genus Gordona: *Gordona rubro* JCM 3199, etc., the genus Rhodococcus: *Rhodococcus equi* JCM 6820, *Rhodococcus sp.* JCM 6832, *Rhodococcus maris* JCM 6167, *Rhodococcus fascians* JCM 1316, *Rhodococcus erythropolis* IFO 12540, *Rhodococcus rhodochrous* DSM 43008, *Rhodococcus coprophilus* DSM 43302, *Rhodococcus terrae* DSM 43342, etc., the genus Aspergillus: *Aspergillus niger* IFO 4415, *Aspergillus ficuum* IFO 4320, etc., the genus Emericella: *Emericella midulans* IAM 2086, etc., the genus Absidia: *Absidia coerulea* JCM 5598, etc., the genus Fusarium: *Fusarium solani* IFO 5232, etc., the genus Dactylium: *Dactylium dendroides* ATCC 46032, etc., the genus Serratia: *Serratia sp.* No. 2664, *Serratia sp.* No. 2666, etc., the genus Pseudomonas: *Pseudomonas Putida* No. 2145B, etc., and the like.

At least one strain of microorganism among them can be employed.

The microorganisms identified hereinabove by IFO numbers are described in the "List of Cultures Ed. 8, Vol. 1 (1988)" published by Institute for Fermentation, Osaka (IFO), Japan and are available from the same Institute. The microorganisms designated by AHU numbers are listed in "Catalogue of Cultures Ed. 4 (1987)" published by Japan Federation of Culture Collections (JFCC) and are available from Faculty of Agriculture, Hokkaido University, Japan. The microorganisms designated by JCM numbers are listed in "Catalogs of Microbial Strains Ed. 4 (1989)" published by the Culture Collection of The Institute of Physical and Chemical Research, Japan and available from the same Culture Collection. The microorganisms designated by DSM numbers are listed in "Catalogs of Strains (1989)" of Deatsche Sammlung von Mikroorganismen (DSM) and are available from the same organization. The microorganisms designated by ATCC numbers have been deposited with American Type Culture Collection (ATCC) and are available from the same organization.

*Serratia sp.* No. 2664, *Serratia sp.* No. 2666 and *Pseudomonas putida* No. 2145B are novel strains which the present inventors have isolated from soil samples. All of these bacterial strains have been deposited with Fermentation Research Institute of the Agency of Industrial Science and Technology (Communications to be addressed to Director of Fermentation Research Institute, the Agency of Industrial Science and Technology) as of May 22, 1991. The accession number of Serratia sp. No. 2664 is FERM P-12268, that of *Serratia sp.* No. 2666 is FERM P-12269 and that of *Pseudomonas putida* No. 2145B is FERM P-12270. *Serratia sp.* No. 2664, *Serratia sp.* 2666, and *Pseudomonas putida* No. 2145B were also deposited on Jun. 3, 1993 with the International Depository Authority of the National Institute of Bioscience and Human-Technology Agency of Industrial Science and Technology, 1–3 Higashi 1 chome, Tsukuba-shi, Ibaraki-ken 305, Japan, and have been given accession numbers FERM BP-4319, FERM BP-4320, and FERM BP-4321, respectively. The bacteriological characteristics and identifications of these strains are as follows.

| Serratia sp. No. 2664 | |
|---|---|
| (a) Morphology | |
| (1) Cell shape and size 0.5–0.7 μm × 1.2–3.0 μm | Rod |
| (2) Motility | Motile |
| (3) Sporulation | Non-sporulating |
| (4) Gram's stain | Negative |
| (b) Physiological characteristics | |
| (1) Oxidase | Negative |
| (2) Catalase | Positive |
| (3) Aminopeptidase | Positive |
| (4) Indole production | Negative |
| (5) VP test | Positive |
| (6) Denitrification | Positive |
| (7) Reduction of nitrate | Positive |
| (8) Citric acid utilization (Simons') | Positive |
| (9) Urease | Positive |
| (10) Phenylalanine deaminase | Negative |
| (11) Malonic acid utilization | Negative |
| (12) Levan formation from sucrose | Negative |
| (13) Lecithinase | Positive |
| (14) Starch hydrolysis | Negative |
| (15) Gelatin hydrolysis | Positive |
| (16) Casein hydrolysis | Positive |
| (17) DNA hydrolysis | Positive |
| (18) Tween 80 hydrolysis | Positive |
| (19) Esculin hydrolysis | Positive |
| (20) Lysis by 3% KOH | Positive |
| (21) Aerobicity | Facultatively anaerobic |
| (22) Growth at 37° C. | Positive |
| (23) Growth at 41° C. | Positive |
| (24) Growth at pH 5.6 | Positive |
| (25) Growth on Mac-Conkey Agar | Positive |
| (26) Growth on SS Agar | Positive |
| (27) Pigment production | Not produced |
| (28) OF test | F |
| (29) Gas production from glucose | — |

Serratia sp. No. 2664 -continued

(30) Acid production from sugars

| | |
|---|---|
| Glucose | + |
| Fructose | + |
| Xylose | + |
| Rhamnose | – |
| Sucrose | + |
| L-Arabinose | + |
| Melibiose | + |
| Trehalose | + |
| Lactose | – |
| Raffinose | – |
| Mannose | + |
| Maltose | + |
| Cellobiose | – |
| Melezitose | – |
| Adonitol | + |
| Inositol | + |
| Mannitol | + |
| Dulcitol | – |
| Sorbitol | + |
| Erythritol | – |
| Salicin | + |
| Glycerol | + |

| | |
|---|---|
| (31) ONPG (β-galactosidase) | Positive |
| (32) Arginine dihydrolase | Negative |
| (33) Lysine decarboxylase | Positive |
| (34) Ornithine decarboxylase | Positive |
| (35) Utilization of carbon sources | |
| Adipic acid | – |
| Caproic acid | + |
| Citric acid | + |
| Hippuric acid | – |
| Maleic acid | + |
| Phenylacetic acid | + |
| Glucose | + |
| Mannose | + |
| Maltose | + |
| Raffinose | – |
| Cellobiose | – |
| Adonitol | + |
| Mannitol | + |
| Nicotinic acid | – |

Comparison of the above bacteriological characteristics with the relevant descriptions in Bergy's Manual of Systematic Bacteriology (1986) suggested that the above strain belongs to the genus Serratia. The strain was accordingly named *Serratia sp.* No. 2664.

Serratia sp. No. 2666

(a) Morphology

| | |
|---|---|
| (1) Cell shape and size | Rod |
| 0.5–0.7 μm × 1.2–3.0 μm | |
| (2) Motility | Motile |
| (3) Sporulation | Non-sporulating |
| (4) Gram's stain | Negative |

(b) Physiological characteristics

| | |
|---|---|
| (1) Oxidase | Negative |
| (2) Catalase | Positive |
| (3) Aminopeptidase | Positive |
| (4) Indole production | Negative |
| (5) VP test | Positive |
| (6) Denitrification | Positive |
| (7) Reduction of nitrate | Positive |
| (8) Citric acid utilization (Simons') | Positive |
| (9) Urease | Negative |
| (10) Phenylalanine deaminase | Negative |
| (11) Malonic acid utilization | Negative |
| (12) Levan formation from sucrose | Negative |
| (13) Lecithinase | Positive |

Serratia sp. No. 2666 -continued

| | |
|---|---|
| (14) Starch hydrolysis | Negative |
| (15) Gelatin hydrolysis | Positive |
| (16) Casein hydrolysis | Positive |
| (17) DNA hydrolysis | Positive |
| (18) Tween 80 hydrolysis | Positive |
| (19) Esculin hydrolysis | Positive |
| (20) Lysis by 3% KOH | Positive |
| (21) Aerobicity | Facultatively anaerobic |
| (22) Growth at 37° C. | Positive |
| (23) Growth at 41° C. | Positive |
| (24) Growth at pH 5.6 | Positive |
| (25) Growth on Mac-Conkey Agar | Positive |
| (26) Growth on SS Agar | Positive |
| (27) Pigment production | Not produced |
| (28) OF test | F |
| (29) Gas production from glucose | – |

(30) Acid production from sugars

| | |
|---|---|
| Glucose | + |
| Fructose | + |
| Xylose | + |
| Rhamnose | – |
| Sucrose | + |
| L-Arabinose | + |
| Melibiose | + |
| Trehalose | + |
| Lactose | – |
| Raffinose | – |
| Mannose | + |
| Maltose | + |
| Melezitose | – |
| Adonitol | + |
| Inositol | + |
| Mannitol | + |
| Dulcitol | – |
| Sorbitol | – |
| Erythritol | – |
| Salicin | + |
| Glycerol | + |

| | |
|---|---|
| (31) ONPG (β-galactosidase) | Positive |
| (32) Arginine dihydrolase | Negative |
| (33) Lysine decarboxylase | Positive |
| (34) Ornithine decarboxylase | Positive |
| (35) Utilization of carbon sources | |
| Adipic acid | – |
| Caproic acid | + |
| Citric acid | + |
| Hippuric acid | – |
| Maleic acid | + |
| Phenylacetic acid | + |
| Glucose | + |
| Mannose | + |
| Maltose | + |
| Raffinose | – |
| Cellobiose | – |
| Adonitol | + |
| Mannitol | + |
| Nicotinic acid | + |

Comparison of the above bacteriological characteristics with the relevant descriptions in Bergy's Manual of Systematic Bacteriology (1986) suggested that the above strain belongs to the genus Serratia. The strain was accordingly named *Serratia sp.* No. 2666.

Pseudomonas Putida No. 2145B (a) Morphology

| | |
|---|---|
| (1) Cell shape and size | |
| 0.5–0.8 μm × 1.5–3.0 μm | |
| (2) Motility | Motile |
| (3) Sporulation | Non-sporulating |

-continued

Pseudomonas Putida No. 2145B

| | | |
|---|---|---|
| (4) | Gram's stain | Negative |
| (5) | Flagellum | Polar (≧1) |
| (b) | Physiological characteristics | |
| (1) | Oxidase | Positive |
| (2) | Catalase | Positive |
| (3) | Aminopeptidase | Positive |
| (4) | Indole production | Negative |
| (5) | VP test | Negative |
| (6) | Denitrification | Negative |
| (7) | Reduction of nitrate | Negative |
| (8) | Urease | Negative |
| (9) | Phenylalanine deaminase | Negative |
| (10) | Levan formation from sucrose | Negative |
| (11) | Lecithinase | Negative |
| (12) | Starch hydrolysis | Negative |
| (13) | Gelatin hydrolysis | Negative |
| (14) | Casein hydrolysis | Negative |
| (15) | DNA hydrolysis | Negative |
| (16) | Tween 80 hydrolysis | Negative |
| (17) | Esculin hydrolysis | Negative |
| (18) | Tyrosine decomposition | Negative |
| (19) | Lysis by 3% KOH | Positive |
| (20) | Aerobicity | Aerobic |
| (21) | Growth at 37° C. | Positive |
| (22) | Growth at 41° C. | Negative |
| (23) | Growth at pH 5.6 | Positive |
| (24) | Growth on Mac-Conkey Agar | Positive |
| (25) | Growth on SS Agar | Positive |
| (26) | Growth on Cetrimid Agar | Positive |
| (27) | Pigment Production | Produced |
| (28) | OF test | O |
| (29) | Gas production from glucose | − |
| (30) | Acid production from sugars | |
| | Glucose | + |
| | Fructose | + |
| | Xylose | + |
| (31) | ONPG (β-galactosidase) | Negative |
| (32) | Arginine dihydrolase | Positive |
| (33) | Growth factor requirement | Negative |
| (34) | Utilization of carbon sources | |
| | Acetic acid | − |
| | Adipic acid | − |
| | Caproic acid | + |
| | Citric acid | + |
| | Citraconic acid | − |
| | Glycolic acid | + |
| | Levulinic acid | − |
| | Maleic acid | + |
| | Malonic acid | + |
| | D/L mandelic acid | − |
| | Phenylacetic acid | + |
| | Sebacic acid | − |
| | L-Tartaric acid | + |
| | L-Arabinose | + |
| | Trehalose | − |
| | Fructose | + |
| | Glucose | + |
| | Mannose | + |
| | Maltose | + |
| | Xylose | − |
| | Mannitol | + |
| | Sorbitol | − |
| | Gluconic acid | + |
| | 2-Ketogluconic acid | + |
| | N-Acetylglucosamine | + |
| | Glycine | − |
| | D-Tryptophan | − |
| | L-Tryptophan | − |
| | Hippuric acid | − |
| | Benzoyl formate | − |
| | Benzylamine | + |

Comparison of the above bacteriological characteristics with the relevant descriptions in Bergy's Manual of Systematic Bacteriology (1986) suggested that the above strain belongs to *Pseudomonas putida*. The strain was accordingly named *Pseudomonas putida* No. 2145B.

For the purposes of the invention, any of wild strains, mutants and recombinant strains which can be obtained by a genetic engineering technique such as cell fusion or gene manipulation, that is able to act on a mixture of enantiomers of 3-phenyl-1,3-propanediol to selectively leave an optically active compound can be advantageously employed.

A microorganism, such as the above, is usually grown in a culture medium and, then, submitted to the reaction with a mixture of enantiomers of 3-phenyl-1,3-propanediol.

The medium which is used for growing the strain for use in the invention is not crital in composition only if the selected strain may grow and multiply therein. The medium is generally a fluid medium containing sources of carbon and nitrogen and other nutrients. Any carbon source which the strain can utilize may be employed. As the sources of carbon, there may be employed various carbohydrates such as glucose, fructose, sucrose, dextrin, starch, etc., alcohols such as sorbitol, ethanol, glycerol, etc., organic acids such as fumaric acid, citric acid, acetic acid, propionic acid, etc. and the corresponding salts, hydrocarbons such as paraffin, and various mixtures thereof. The sources of nitrogen include, among others, inorganic acid ammonium salts such as ammonium chloride, ammonium sulfate, ammonium phosphate, etc., organic acid ammonium salts such as ammonium fumarate, ammonium citrate, etc., inorganic or organic nitrogenous materials such as meat extract, yeast extract, malt extract, peptone, corn steep liquor, casein hydrolysate, urea, etc., and various mixtures thereof. In the medium, there may be incorporated appropriate amounts of those nutrients which are commonly employed in the cultivation of microorganisms, such as inorganic salts, trace metal salts and vitamins. Where necessary, there may also be incorporated factors which may promote growth of the strain used and/or factors which may augment its ability to produce the object compound of the invention, such as a mixture of enantiomers of 3-phenyl-1,3-propanediol, as well as a buffer substance which may assist in the maintenance of the medium at a given pH.

The cultivation of the microorganism is carried out under conditions optimal for the growth of the particular strain, for example at a medium pH in the range of about 3.0 to 9.5, preferably about 4 to 8, and an incubation temperature in the range of about 20° to 45° C., preferably about 25° to 37° C. The cultivation may be aerobic or anaerobic. The cultivation time may, for example, be 5 to 120 hours, preferably about 12 to 72 hours.

The proportions of (R) and (S) in the substrate mixture of enantiomers of 3-phenyl-1,3-propanediol are not critical but it is advantageous for commercial purposes to employ a racemic form of 3-phenyl-1,3-propanediol.

The desired optically active 3-phenyl-1,3-propanediol is produced as a mixture of enantiomers of 3-phenyl-1,3-propanediol is added to a cell dispersion of the microorganism. The method of production of optically active 3-phenyl-1,3-propanediol from a mixture of enantiomers of 3-phenyl-1,3-propanediol may, for example, be whichever of the following alternatives: the method which comprises adding a mixture of enantiomers to a culture broth as such and the method which comprises separating the microbial cells from the culture broth, e.g. by centrifugation, resuspending the cells, either as they are or after washing with water, in a buffer solution, water or the like, and adding a mixture of enantiomers of 3-phenyl-1,3-propanediol to the resulting cell suspension. There are cases in which this reaction proceeds with advantage in the presence of a carbon source, such as glucose or sucrose, which serves as an energy source.

The optimal cell concentration of the reaction system cannot be stated in general terms, for it is significantly dependent on the species or strain of microorganism employed. However, the concentration should be in the range where the efficiency of leaving the desired optically active compound intact will not be adversely affected. A typical cell concentration may for example be, on a dry cell basis, about 0.1 to 100 g/liter and preferably about 1 to 50 g/liter.

The cells may be wet viable cells or any preparation thereof, such as disrupted cells, acetone-treated cells, lyophilized cells and so on. These cells or cell preparations may be immobilized by known techniques such as the polyacrylamide gel method, sulfur-containing polysaccharide gel method (e.g. carrageenin gel method), alginic acid gel method, agar gel method and so on. The enzyme purified from such a cell preparation can also be employed. The enzyme can be obtained by using known purification processes in a suitable combination.

The mixture of enantiomers of 3-phenyl-1,3-propanediol can be used as it is or in the form of a solution in water or an organic solvent which will not interfere with the reaction or a dispersion prepared with a surfactant. The mixture of enantiomers of 3-phenyl-1,3-propanediol may be added in bolus at the beginning of the reaction or in several installments.

The reaction conditions can be selected from the ranges that will not detract from the yield of the object compound. For example, the pH of the reaction system can be selected from the range of pH about 3 to 10 and preferably pH about 5 to 9. The reaction temperature can be selected from the range of, for example, 10° to 60° C. and preferably from 20° to 40° C. The reaction can be conducted with stirring or under stationary conditions for about 1 to 120 hours. As a tendency, the longer the reaction time, the smaller the residual amount of the desired 3-phenyl-1,3-propanediol compound but the higher is the optical purity of the 3-phenyl-1,3-propanediol. The concentration of a mixture of enantiomers of 3-phenyl-1,3-propanediol as the substrate is not particularly critical and is preferably about 0.1 to 20 weight % and more preferably about 0.2 to 10 weight %.

The optically active 3-phenyl-1,3-propanediol produced by the reaction, which remains in the reaction system, can be harvested by the separation and purification procedures generally known. For example, the optically active 3-phenyl-1,3-propanediol can be easily obtained by subjecting the reaction mixture, directly or after separation of the cells, to the conventional purification procedure such as extraction with an organic solvent, distillation and column chromatography. The optical purity of optically active 3-phenyl-1,3-propanediol can be measured by high performance liquid chromatography (HPLC) using an optical resolution column.

INDUSTRIAL APPLICABILITY

The optically active 3-phenyl-1,3-propanediol obtainable by the process of the invention is of value, for example as an important intermediate for the synthesis of tomoxethine which is an anti-depressant agent.

The following examples are intended to illustrate the invention in further detail and should by no means be construed as delimiting the scope of the invention.

EXAMPLES

In the examples, the quantitative and optical purity determinations of 3-phenyl-1,3-propanediol in reaction mixtures were carried out by subjecting the optically active 3-phenyl-1,3-propanediol obtained by the reaction directly to high performance liquid chromatography using an optical resolution column (column: Chiralcel OB, Daicel Chemical Industries, Ltd.; solvent: n-hexane-isopropyl alcohol=19:1; wavelength: 254 nm; flow rate: 1.0 ml/min.; column temperature: 40° C.; injection volume: 10 μl ). Under the above operating conditions, the reaction time of 3-phenyl-1,3-propanediol was 13.1 minutes for (S) and 16.4 minutes for (R).

EXAMPLE 1

A 500-ml Sakaguchi flask was charged with 50 ml of the following growth medium and, after sterilization, was inoculated with one of the microbial stains shown in Table 1. The inoculated flask was incubated under shaking at 30° C. for 48 hours.

| Growth medium | |
| --- | --- |
| Glucose | 2.0 weight % |
| Yeast extract | 0.3 weight % |
| Peptone | 0.5 weight % |
| Malt extract | 0.3 weight % |
| pH | 6.0 |

Then, 0.25 g of racemic 3-phenyl-1,3-propanediol was added to the culture broth containing the cells and the reaction was conducted on a reciprocating shaker at 30° C. for 96 hours.

After completion of the reaction, the cells were removed from the reaction mixture by centrifugation and the supernatant was extracted with 50 ml of ethyl acetate. The ethyl acetate extract was dehydrated over anhydrous sodium sulfate and the solvent was removed to give a syrup.

The syrup was dissolved in 50 ml of hexane-isopropyl alcohol (50/50) and the residual amount, absolute configuration and optical purity of the optically active 3-phenyl-1,3-propanediol were determined. The results are set forth in Table 1.

TABLE 1

| Name of Microorganism | Absolute configuration | Optical purity (% e.e.) | Residual amount of 3-phenyl-1,3-propanediol (mg) |
| --- | --- | --- | --- |
| Candida pintolopesii var. pintolopesii IFO 0729 | S | 95 | 100 |
| Geotrichum candidum IFO 4597 | S | 95 | 120 |
| Geotrichum candidum II 4598 | S | 91 | 120 |
| Geotrichum candidum IFO 5368 | S | 94 | 110 |
| Geotrichum candidum IFO 31810 | S | 55 | 160 |
| Geotrichum candidum JCM 1747 | S | 71 | 140 |
| Geotrichum candidum JCM 5222 | S | 63 | 140 |
| Geotrichum fermentans JCM 2467 | S | 56 | 150 |
| Geotrichum fermentans | S | 90 | 120 |

TABLE 1-continued

| Name of Microorganism | Absolute configuration | Optical purity (% e.e.) | Residual amount of 3-phenyl-1,3-propanediol (mg) |
|---|---|---|---|
| JCM 2468 | | | |
| Geotrichum kiebahnii JCM 2171 | S | 95 | 90 |
| Leucosporidium scottii IFO 1923 | S | 43 | 110 |
| Pichia quercuum DSM 70386 | S | 59 | 160 |
| Torulaspora delbrueckii IFO 0955 | S | 74 | 120 |
| Trichosporon capitatum IFO 1197 | S | 80 | 120 |
| Candida lambica DSM 70090 | R | 95 | 100 |
| Hansenula minuta DSM 70274 | R | 58 | 150 |
| Rhodotorula rubra AHU 3945 | R | 81 | 120 |
| Rhodotorula rubra AHU 3948 | R | 89 | 120 |

EXAMPLE 2

A 500-ml Sakaguchi flask was charged with 50 ml of the following growth medium and, after sterilization, was inoculated with one of the strains mentioned in Table 2. The inoculated flask was incubated under shaking at 30° C. for 48 hours.

| Growth medium | |
|---|---|
| Meat extract | 1.0 weight % |
| Peptone | 1.0 weight % |
| Sodium chloride | 0.5 weight % |
| pH | 7.3 |

Then, 0.25 g of racemic 3-phenyl-1,3-propanediol was added to the culture broth containing the cells and the reaction was conducted on a reciprocating shaker at 30° C. for 48 hours. After completion of the reaction, the residual amount, absolute configuration and optical purity of 3-phenyl-1,3-propanediol were determined as in Example 1. The results are set forth in Table 2.

TABLE 2

| Name of Microorganism | Absolute configuration | Optical purity (% e.e.) | Residual amount of 3-phenyl-1,3-propanediol (mg) |
|---|---|---|---|
| Protaminobacter ruber IAM 1081 | R | 74 | 100 |
| Escherichia con IFO 3543 | S | 90 | 90 |
| Micrococcus luteus IFO 12708 | S | 48 | 100 |
| Corynebacterium hoagii JCM 1319 | S | 94 | 70 |
| Gordona rubro JCM 3199 | S | 100 | 80 |
| Rhodococcus equi JCM 6820 | S | 100 | 90 |
| Rhodococcus sp. JCM 6832 | S | 100 | 90 |

TABLE 2-continued

| Name of Microorganism | Absolute configuration | Optical purity (% e.e.) | Residual amount of 3-phenyl-1,3-propanediol (mg) |
|---|---|---|---|
| Rhodococcus maris JCM 6167 | S | 87 | 100 |
| Rhodococcus fascians JCM 1316 | S | 100 | 80 |
| Rhodococcus erythropolis IFO 12540 | S | 87 | 100 |
| Rhodococcus rhodochrous DSM 43008 | S | 100 | 70 |
| Rhodococcus coprophilus DSM 43302 | S | 74 | 100 |
| Rhodococcus terrae DSM 43342 | S | 100 | 70 |

EXAMPLE 3

The same procedures as in Example 1 were performed except that a 500-ml Sakaguchi flask was charged with 50 ml of the following growth medium and, after sterilization, was inoculated with one of the strains mentioned in Table 3. The residual amount, absolute configuration and optical purity of 3-phenyl-1,3-propanediol were determined as in Example 1. The results are set forth in Table 3.

| Growth medium | |
|---|---|
| Potato (200 g) infusion | 1000 ml |
| Glucose | 20 g |
| Yeast extract | 2 g |
| pH | 5.6 |

TABLE 3

| Name of Microorganism | Absolute configuration | Optical purity (% e.e.) | Residual amount of 3-phenyl-1,3-propanediol (mg) |
|---|---|---|---|
| Aspergillus niger IFO 4414 | R | 64 | 5.0 |
| Aspergillus ficuum IFO 4318 | R | 40 | 5.2 |
| Alternaria kikuchiana IFO 5778 | R | 46 | 6.3 |
| Macrophomina phaseoli IFO 6696 | R | 46 | 6.5 |
| Preussia terricola IFO 7893 | R | 42 | 6.5 |
| Talaromyces flavus var. flavus IFO 7231 | R | 89 | 4.6 |
| Aspergillus niger IFO 4415 | S | 44 | 6.8 |
| Aspergillus ficuum IFO 4320 | S | 82 | 4.4 |
| Emericella midulans IAM 2086 | S | 60 | 5.2 |
| Absidia coerulea JCM 5598 | S | 66 | 6.6 |
| Fusarium solani IFO 5232 | S | 78 | 5.0 |
| Dactylium dendroides ATCC 46032 | S | 50 | 6.8 |

EXAMPLE 4

A 2-liter Sakaguchi flask was charged with 500 ml of a medium (pH 7) containing 1% of glucose, 0.5% of yeast extract, 0.3% of polypeptone, 0.2% of ammonium sulfate and 0.05% of magnesium sulfate heptahydrate and heat-sterilized. This medium was inoculated with *Serratia sp.* No. 2664 and incubated on a reciprocal shaker at 30° C. for 24 hours. The resulting broth was centrifuged to separate the cells, which were washed with physiological saline solution. The cells were resuspended in sufficient water to make 95 ml and the suspension was put in a 500-ml Sakaguchi flask. Then, 5 ml of a 20% (w/v) aqueous solution of recemic 3-phenyl-1,3-propanediol was added and the mixture was incubated on a reciprocating shaker at 30° C. for 72 hours. After completion of the reaction, the culture broth was centrifuged to separate the cells and the supernatant extracted twice with 100 ml portions of ethyl acetate. The organic layers were pooled and dehydrated over anhydrous sodium sulfate and the solvent was evaporated off to give a syrup.

The syrup was dissolved in 10 ml of hexane-isopropyl alcohol (50:50) and the yield, absolute configuration and optically purify of the optically active 3-phenyl-1,3-propanediol were determined as in Example 1. The yield was found to be 37%, the absolute configuration to be S, and the optical purity to be 96% e.e.

EXAMPLE 5

The cultivation, reaction and purification procedures of Example 4 were repeated except that *Serratia sp.* No. 2666 was used in lieu of *Serratia sp.* No. 2664 and the product was analyzed. The yield was found to be 40%, the absolute configuration to be S, and the optical purity to be 98% e.e.

EXAMPLE 6

The cultivation, reaction and purification procedures of Example 4 were repeated except that *Pseudomonas putida* No. 2145B was used in lieu of *Serratia sp.* No. 2664 and the product was analyzed. The yield was found to be 38%, the absolute configuration to be S, and the optical purity to be 90% e.e.

We claim:

1. A biologically pure culture of *Serratia sp.* No. 2664 (FERM BP-4319) which is capable of increasing the optical purity of (S)-3-phenyl-1,3-propanediol from a mixture of (R) and (S) enantiomers of 3-phenyl-1,3-propanediol.

2. A biologically pure culture of *Serratia sp.* No. 2666 (FERM BP-4320) which is capable of increasing the optical purity of (S)-3-phenyl-1,3-propanediol from a mixture of (R) and (S) enantiomers of 3-phenyl-1,3-propanediol.

3. A biologically pure culture of *Serratia sp.* No. 2664 (FERM BP-4319) comprising the morphological characteristics of:

| | |
|---|---|
| Cell shape | Rod |
| Cell size | From about 0.5 to 0.7 μm by about 1.2 to 3.0 μm |
| Motility | Motile |
| Sporulation | Non-sporulating |
| Gram's stain | Negative | and the physiological characteristics of:

| | |
|---|---|
| Oxidase | Negative |
| Catalase | Positive |
| Aminopeptidase | Positive |
| Indole production | Negative |
| VP test | Positive |
| Denitrification | Positive |
| Reduction of nitrate | Positive |
| Citric acid utilization | Positive |
| Urease | Positive |
| Phenylalanine deaminase | Negative |
| Malonic acid utilization | Negative |
| Levan formation from sucrose | Negative |
| Lecithinase | Positive |
| Starch hydrolysis | Negative |
| Gelatin hydrolysis | Positive |
| Casein hydrolysis | Positive |
| DNA hydrolysis | Positive |
| Tween 80 hydrolysis | Positive |
| Esculin hydrolysis | Positive |
| Lysis by 3% KOH | Positive |
| Aerobicity | Facultatively Anerobic |
| Growth at 37° C. | Positive |
| Growth at 41° C. | Positive |
| Growth at pH 5.6 | Positive |
| Growth on MacConkey agar | Positive |
| Growth on SS agar | Positive |
| Pigment production | Not Produced |
| OF test | F |
| Gas production from glucose | Negative |
| Acid production from glucose | Positive |
| Acid production from fructose | Positive |
| Acid production from xylose | Positive |
| Acid production from rhamnose | Negative |
| Acid production from sucrose | Positive |
| Acid production from L-arabinose | Positive |
| Acid production from melibiose | Positive |
| Acid production from trehalose | Positive |
| Acid production from lactose | Negative |
| Acid production from raffinose | Negative |
| Acid production from mannose | Positive |
| Acid production from maltose | Positive |
| Acid production from cellobiose | Negative |
| Acid production from melezitose | Negative |
| Acid production from adonitol | Positive |
| Acid production from inositol | Positive |
| Acid production from mannitol | Positive |
| Acid production from dulcitol | Negative |
| Acid production from sorbitol | Positive |
| Acid production from erythritol | Negative |
| Acid production from salicin | Positive |
| Acid production from glycerol | Positive |
| ONPG (β-galactosidase) | Positive |
| Arginine dihydrolase | Negative |
| Lysine decarboxylase | Positive |
| Ornithine decarboxylase | Positive |
| Utilization of adipic acid | Negative |
| Utilization of caproic acid | Positive |
| Utilization of citric acid | Positive |
| Utilization of hippuric acid | Negative |
| Utilization of maleic acid | Positive |
| Utilization of phenylacetic acid | Positive |
| Utilization of glucose | Positive |
| Utilization of mannose | Positive |
| Utilization of maltose | Positive |
| Utilization of raffinose | Negative |
| Utilization of cellobiose | Negative |
| Utilization of adonitol | Positive |
| Utilization of mannitol and | Positive |
| Utilization of nicotinic Acid | Negative. |

4. A biologically pure culture of *Serratia sp.* No. 2666 (FERM BP-4320) comprising the morphological characteristics of:

| | |
|---|---|
| Cell shape | Rod |
| Cell size | From about 0.5 to 0.7 μm by about 1.2 to 3.0 μm |
| Motility | Motile |

| | |
|---|---|
| Sporulation | Non-sporulating |
| Gram's stain | Negative | and the physiological characteristics of:

| | |
|---|---|
| Oxidase | Negative |
| Catalase | Positive |
| Aminopeptidase | Positive |
| Indole production | Negative |
| VP test | Positive |
| Denitrification | Positive |
| Reduction of nitrate | Positive |
| Citric acid utilization | Positive |
| Urease | Negative |
| Phenylalanine deaminase | Negative |
| Malonic acid utilization | Negative |
| Levan formation from sucrose | Negative |
| Lecithinase | Positive |
| Starch hydrolysis | Negative |
| Gelatin hydrolysis | Positive |
| Casein hydrolysis | Positive |
| DNA hydrolysis | Positive |
| Tween 80 hydrolysis | Positive |
| Esculin hydrolysis | Positive |
| Lysis by 3% KOH | Positive |
| Aerobicity | Facultatively Anerobic |
| Growth at 37° C. | Positive |
| Growth at 41° C. | Positive |
| Growth at pH 5.6 | Positive |
| Growth on MacConkey agar | Positive |
| Growth on SS agar | Positive |
| Pigment production | Not Produced |
| OF test | F |
| Gas production from glucose | Negative |
| Acid production from glucose | Positive |
| Acid production from fructose | Positive |
| Acid production from xylose | Positive |
| Acid production from rhamnose | Negative |
| Acid production from sucrose | Positive |
| Acid production from L-arabinose | Positive |
| Acid production from melibiose | Positive |
| Acid production from trehalose | Positive |
| Acid production from lactose | Negative |
| Acid production from raffinose | Negative |
| Acid production from mannose | Positive |
| Acid production from maltose | Positive |
| Acid production from melezitose | Negative |
| Acid production from adonitol | Positive |
| Acid production from inositol | Positive |
| Acid production from mannitol | Positive |
| Acid production from dulcitol | Negative |
| Acid production from sorbitol | Negative |
| Acid production from erythritol | Negative |
| Acid production from salicin | Positive |
| Acid production from glycerol | Positive |
| ONPG (β-galactosidase) | Positive |
| Arginine dihydrolase | Negative |
| Lysine decarboxylase | Positive |
| Ornithine decarboxylase | Positive |
| Utilization of adipic acid | Negative |
| Utilization of caproic acid | Positive |
| Utilization of citric acid | Positive |
| Utilization of hippuric acid | Negative |
| Utilization of maleic acid | Positive |
| Utilization of phenylacetic acid | Positive |
| Utilization of glucose | Positive |
| Utilization of mannose | Positive |
| Utilization of maltose | Positive |
| Utilization of raffinose | Negative |
| Utilization of cellobiose | Negative |
| Utilization of adonitol | Positive |
| Utilization of mannitol and | Positive |
| Utilization of nicotinic acid | Positive. |

\* \* \* \* \*